US008382476B2

(12) United States Patent
Schulte et al.

(10) Patent No.: US 8,382,476 B2
(45) Date of Patent: Feb. 26, 2013

(54) DENTAL RETRACTION COMPOSITION, PRODUCTION THEREOF AND USE OF A POWDER JET DEVICE FOR DENTAL RETRACTION

(75) Inventors: Christoph Schulte, Windach (DE); Andreas R. Maurer, Langenneufnach (DE); Thomas Klettke, Diessen (DE); Ruediger Hampe, Landsberg (DE); Ingo R. Haeberlein, Weilheim (DE)

(73) Assignee: 3M Innovative Properties Company, Saint Paul, MN (US)

( * ) Notice: Subject to any disclaimer, the term of this patent is extended or adjusted under 35 U.S.C. 154(b) by 105 days.

(21) Appl. No.: 12/747,219

(22) PCT Filed: Dec. 9, 2008

(86) PCT No.: PCT/US2008/086013
§ 371 (c)(1),
(2), (4) Date: Jun. 10, 2010

(87) PCT Pub. No.: WO2009/076332
PCT Pub. Date: Jun. 18, 2009

(65) Prior Publication Data
US 2010/0261136 A1 Oct. 14, 2010

(30) Foreign Application Priority Data
Dec. 10, 2007 (EP) ..................................... 07122768

(51) Int. Cl.
*A61C 3/02* (2006.01)
(52) U.S. Cl. .......................................... 433/88; 433/215
(58) Field of Classification Search .................... 433/88, 433/215; 514/951, 952; 264/123
See application file for complete search history.

(56) References Cited

U.S. PATENT DOCUMENTS

| 3,972,123 A | 8/1976 | Black |
| 4,232,688 A | 11/1980 | Day |
| 4,260,597 A | 4/1981 | Porteous |
| 4,321,038 A | 3/1982 | Porteous |
| 4,465,462 A | 8/1984 | Ticknor |
| 4,522,593 A | 6/1985 | Fischer |
| 4,597,960 A | 7/1986 | Cohen |
| 4,617,950 A | 10/1986 | Porteous et al. |
| 4,676,749 A | 6/1987 | Mabille |
| 4,836,853 A * | 6/1989 | Gribi ................ 106/35 |
| 4,854,867 A | 8/1989 | Meinershagen |
| 4,871,311 A | 10/1989 | Hange |
| 4,892,482 A | 1/1990 | Lococo |
| 5,120,219 A * | 6/1992 | De Farcy ........................ 433/88 |
| 5,358,403 A | 10/1994 | Groth |
| 5,362,495 A | 11/1994 | Lesage |
| 5,480,303 A | 1/1996 | Groth |
| 5,540,588 A | 7/1996 | Earle |
| 5,635,162 A | 6/1997 | Fischer |
| 5,785,955 A | 7/1998 | Fischer |
| 5,899,694 A | 5/1999 | Summer |
| 5,976,439 A | 11/1999 | Mahoney |
| 6,116,905 A | 9/2000 | Hoos |
| 6,375,461 B1 | 4/2002 | Jensen et al. |
| 6,568,398 B2 | 5/2003 | Cohen |
| 6,575,749 B1 | 6/2003 | Greenwald |
| 6,648,644 B1 * | 11/2003 | Flemmig et al. ............... 433/216 |
| 7,083,411 B2 * | 8/2006 | Flemmig et al. ................ 433/88 |
| 2004/0202980 A1 * | 10/2004 | Policicchio ..................... 433/88 |
| 2005/0008583 A1 | 1/2005 | White |
| 2005/0069838 A1 | 3/2005 | Kollefrath et al. |
| 2005/0287494 A1 | 12/2005 | Yang et al. |
| 2007/0065770 A1 | 3/2007 | Lubbers et al. |
| 2008/0286719 A1 | 11/2008 | Mueller et al. |
| 2010/0035213 A1 | 2/2010 | Lubbers et al. |

FOREIGN PATENT DOCUMENTS

| DE | 2142756 | 3/1973 |
| EP | 231420 B1 | 9/1991 |
| EP | 1886659 A1 * | 2/2008 |
| GB | 2026359 A | 6/2009 |
| WO | WO 96/14453 | 5/1996 |
| WO | WO 02-074180 A1 | 9/2002 |
| WO | WO 2004/082510 | 9/2004 |
| WO | WO 2005/007095 A2 | 1/2005 |
| WO | WO 2005007095 A2 * | 1/2005 |
| WO | WO 2005/122945 | 12/2005 |
| WO | WO 2006/002939 | 1/2006 |
| WO | WO 2006/057535 | 6/2006 |
| WO | WO 2006/089857 | 8/2006 |
| WO | WO 2009/014453 | 1/2009 |

(Continued)

OTHER PUBLICATIONS

Handbook of Hydrocolloids, Edited by: Phillips, G.O.; Williams, P.A., © 2000 Woodhead Publishing, "Alginates", K. I. Draget, Norwegian University of Science and Technology, Chapter 22, pp. 379-393.

(Continued)

*Primary Examiner* — Chris L Rodriguez
*Assistant Examiner* — Matthew Saunders
(74) *Attorney, Agent, or Firm* — Carlos M. Téllez

(57) ABSTRACT

The invention relates to a dental composition comprising a hardenable powder to be used in a process for retraction of dental tissue. The invention also relates to a kit of parts comprising the dental composition comprising a hardenable powder, a hardening agent, optionally a handpiece of a powder jet device, optionally a powder jet device, and optionally retraction caps. In a further aspect, the invention relates to a method for retracting dental tissue comprising the steps of applying a dental composition comprising a hardenable powder with a powder jet device into the sulcus between soft and hard dental tissue, applying a composition comprising a hardening agent either before or after the previous step, leaving the dental composition in the sulcus for a time sufficient to effect retraction of the soft dental tissue and removing the dental composition from the sulcus.

7 Claims, No Drawings

OTHER PUBLICATIONS

Search Report for EP Application No. 07122768, 5 pages.
Search Report for EP Application No. 08860376, 2 pages.
Search Report for International Application No. PCT/US2008/086013, 3 pages.

Written Opinion for International Application No. PCT/US2008/086013, 6 pages.

* cited by examiner

DENTAL RETRACTION COMPOSITION, PRODUCTION THEREOF AND USE OF A POWDER JET DEVICE FOR DENTAL RETRACTION

CROSS REFERENCE TO RELATED APPLICATIONS

This application is a national stage filing under 35 U.S.C. 371 of PCT/US2008/086013, filed Dec. 9, 2008, which claims priority to European Application No. 07122768.0, filed Dec. 10, 2007, the disclosure of which is incorporated by reference in its entirety herein.

FIELD OF THE INVENTION

The present invention relates to a dental composition comprising a hardenable powder to be used in a process for retraction of dental tissue and the use of a powder jet device for applying a dental composition, especially a dental retraction composition comprising a hardenable powder. The invention also relates to a method for retracting dental tissue using the dental composition comprising a hardenable powder.

BACKGROUND ART

For retracting gingiva from a prepared tooth a cord can be used. In this respect, a retraction cord is packed between gingival tissue and the margin of the prepared tooth (this region is also often called sulcus) using an appropriate dental instrument. To obtain sufficient vertical and horizontal retraction of gingival tissue, it is often necessary to pack several lengths of retraction cord into the sulcus in order to be able to make a detailed dental impression.

A description of the background in regard to retraction cords can be found e.g. in U.S. Pat. No. 4,522,593.

Generally, dental retraction cords are sometimes difficult to place into the gingival sulcus. The procedure can also be time consuming. Moreover, it can be cumbersome to remove the retraction cord prior to taking the impression. Coagulated blood may adhere to the cord and removing it may open the wound again which may result in bleeding.

For a more convenient placement retraction pastes have been suggested.

Non-hardening retraction pastes containing either an anti-evaporating component or fibrillated fibres are described in e.g. US 2005/000853 and US 2005/028749.

U.S. Pat. No. 5,362,495 refers to a method for widening the gingival sulcus comprising inserting within the gingival sulcus a material in the form of a biocompatible paste which is injectable for external use and having a plastic viscosity measured at 20° C. between about 13,000 and 30,000 Pa*s, wherein said material consisting of a material selected from the group of white clay, seaweed meal and mixtures thereof.

US 2005/0069838 discloses a dental kit and method for retraction sulcus using an expanding silicone compound or mixture of different silicone compounds. However, silicone compounds are of inorganic and hydrophobic nature, thus having limited biocompatibility with oral tissue and disadvantages in flowing to moist tissue and tooth surfaces and moist areas like the gingival sulcus.

In DE 2 142 756 a process for producing a retraction ring is described. A dry powder mixture of blood coagulant, local anaestetic and disinfectant is filled in cavities of a ring by applying gas pressure in a sealed chamber under partial vacuum or by applying the powder mixture under ambient conditions to the surface of the ring.

None of the above outlined procedure is fully satisfying to the practitioner.

Thus, there is still room for improvement especially with regard to the requirements to be fulfilled with respect to modern dental materials.

Ideally, a material is desired, that can easily be inserted into the sulcus and around a prepared tooth.

DESCRIPTION OF THE INVENTION

In one aspect the invention features a dental composition comprising a hardenable powder to be used in a process for retraction of dental tissue.

In another aspect, the invention is directed to the use of a hardenable powder for the production of a dental composition to be used in a process for retraction of dental tissue.

A further aspect of the invention is directed to a kit of parts comprising
 a dental composition comprising a hardenable powder,
 a hardening agent, suitable to effect hardening of the hardenable powder
 optionally a handpiece of a powder jet device,
 optionally a powder jet device, and
 optionally retraction caps.

In another aspect the invention features a method of producing a dental retraction composition using a hardenable powder.

The invention is also directed to a method of using a powder jet device for applying or dispensing a dental composition comprising a hardenable powder.

Yet another aspect of the invention is directed to a method for retracting dental tissue comprising the steps of
 a) applying a dental composition comprising a hardenable powder with a powder jet device into the sulcus between soft and hard dental tissue,
 b) applying a composition comprising a hardening agent either before or after step a) especially into the sulcus or onto at least a part of the surface of the dental composition,
 c) leaving the dental composition in the sulcus for a time sufficient to effect retraction of the soft dental tissue,
 d) removing the dental composition from the sulcus.

DEFINITIONS

Within the description of the invention, the following terms are defined as follows:

A "composition" is typically understood to be a mixture of two or more components.

A "dental retraction composition" is a composition enabling the practitioner to retract soft dental tissue (e.g. gingival) away from hard dental tissue (e.g. tooth) before or during an impression of the dental situation in the mouth of a patient is made. The dental retraction composition can also be used whenever a clean and dry working area is required e.g. when placing a restoration or applying a filling composite. In view of the fact, that a dental retraction composition is to be used in the dental field and is typically classified as a medical product, certain requirements with respect to safety and toxicology have to be fulfilled.

A "tooth structure" is any tooth structure, prepared or ready for preparation by the dentist. It can be a single tooth or two or more teeth. A tooth structure is also referred to as hard dental tissue in contrast to soft dental tissue (e.g. gingival).

A composition, component or powder may be described as "hardenable", if the components of the composition are contributing to the formation of a network due to chemical interaction (e.g. formation of chemical bondings) or physical interaction (including electrostatic and/or dipole/dipole interaction) between the components thereby leading to a significant change in rheological properties like viscosity.

A "hardenable composition" is a composition which can be hardened within a reasonable time (e.g. within a couple of minutes or seconds, e.g. up to about 10 min or up to about 5 min or up to about 1 min or up to about 30 s or even up to about 5 s) as soon as the curing process has been started, e.g. by applying a curing or setting agent like a crosslinker or adding an initiator. Curing can also be initiated by light, radiation or temperature. Typically, the setting can be accomplished at ambient conditions, (e.g. about 20 to about 40° C.) without applying external heat.

A "hardening, curing or setting reaction" is a reaction wherein physical properties such as viscosity, stickiness, tensile strength and/or compressive strength of a composition change over the time due to a chemical or physical reaction or interaction between the individual components.

A "poly-, di- or trivalent ion source" is a component or composition which is able to provide ions with the respective charge, if dissolved in a liquid such as water. That is, the polyvalent ion source is able to dissociate into cations having a charge of at least plus two (2+) or at least plus tri (3+) and the respective anions to a certain amount over time.

A "powder jet device" is a device which can be used for the application of a powder or a mixture of powders using a stream of gas, optionally combined with the application of a liquid such as water. Typically, a powder jet device comprises a reservoir for the powder to be applied and optionally a unit being able to provide a stream of gas and optionally a liquid.

An "alginate" is a salt of an alginic acid. Alginates are used for making dental impressions since many years. Alginates are usually delivered as powders and form an irreversible hydrocolloide in the presence of water. The alginic acid is a bio-copolymer containing dehydro-D-mannuronic acid and dehydro-L-guluronic acid. A comprehensive review on alginates which can be used in the dental field can be found in: Handbook of Hydrocolloids, Edited by: Phillips, G. O.; Williams, P. A., ©2000 Woodhead Publishing, Chapter 22. Alginate containing materials are sometimes preferred as these materials are biodegradable and thus lower the risk of infection during and after the treatment should material remain in the sulcus. Alginate pastes typically show good flow properties into the sulcus (due to the hydrophilic nature of the material).

A "hemostatic agent" is an agent which is able to reduce bleeding to a certain amount and/or causes blood to coagulate.

A "dental compositions and dental articles" is a composition which is to be used in the dental field (including prophylactic, restorative prosthodontic work and the orthodontic area). In this respect the composition should be not detrimental to the patient's health and thus free of hazardous and toxic components being able to migrate out of the composition. Commercially available products have to fulfil certain requirements such as those given in EN ISO 13485:2003.

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "powder" is a finely divided substance comprising solid particles, the size of which can be analyzed using a granulometer.

"Liquid" shall comprise every fluid, which can be transported by a powder jet device. Those liquids are mainly comprised of water.

A "paste" is a substance that behaves as a solid until a sufficiently large load or stress is applied, at which point it flows like a fluid. Pastes typically consist of a suspension of granular material in a background fluid. The individual grains are jammed together like sand on a beach, forming a disordered, glassy or amorphous structure, and giving pastes their solid-like character.

A "gel" is typically a colloidal system in which a porous matrix of interconnected particles spans the volume of a liquid medium. In general, gels are apparently solid, jelly-like materials. Both by weight and volume, gels are mostly liquid in composition and thus exhibit densities similar to liquids, however, have the structural coherence of a solid. An example of a common gel is edible gelatin. Many gels display thixotropy, that is, they become fluid when agitated, but resolidify when resting.

The term "soluble in water" means that a substance as such is soluble in water at ambient conditions, comparable to a salt. That is, the substance is able to form individual molecules like glucose when dispersed in water. Thus, water-soluble powders described in the text of the invention typically have a so-called solubility product.

An agent is characterized as being "absorbing", if the agent is able on contact with fluid to suck up a certain amount of the fluid from the surroundings. This usually goes along with an increase in size and volume of the absorbing substance. Depending on the agent chosen, this sometimes goes also along with a change in the surface characteristics. E.g. the surface of the agent might become more slippery or gel-like.

"Anti-microbial agents" may be all anti-microbial compounds, especially those compatible with elastomeric dental materials including alginate and silicone containing impression materials, and if desired also with polyether containing impression materials.

"Network builders" are components which are able to form a network by a crosslinking reaction between the respective components. This network can be an interpenetrating network, that is a network that interferes with the alginate network or it can be a network that exists besides the alginate network without interference.

The particle distribution of a powder can be analyzed using commercially available granulometers (e.g. CILAS1064 Nass Laser Diffraction Particle Size Analysis Instrument).

The term d90/μm with regard to particle size measurement means that in 90% of the analyzed volume, the particles have a size below x μm. E.g., a particle size value of below 100 μm (d90) means that within the analyzed volume, 90% of the particles have a size below 100 μm.

If not otherwise indicated "molecular weight" always means Mw (weight average of the molecular weight) and can be determined for the individual classes of polymers by gel permeation chromatography (GPC) against a standard of defined molecular weight. Suitable measurement methods are known to the person skilled in the art.

The molecular weight of alginates is usually determined by measurement of the viscosity of a defined solution with respect to a calibration curve. The molecular weight of alginates referred to in the invention is based on the information provided by the suppliers.

The term "essentially does not" is to be understood that a certain—sometimes unavoidable—effect does usually not take place or only occurs to a minimum amount, wherein the effect does not negatively affect the overall result to be achieved.

The setting behaviour of a curable composition is "not negatively affected", if the setting of a curable composition takes place within the given specification. Small deviations (e.g. within a range of about 5 to 10%) from given physical parameters like viscosity, working time or setting time, which might occur if e.g. an additive is added or setting takes place in conjunction with other materials or substances (e.g. in the presence of a retraction device), are not considered detrimental.

"Ambient conditions" mean the conditions which the inventive composition is usually subjected to during storage and/or handling. Ambient conditions may, for example, be a pressure of about 700 to about 1100 mbar, a temperature of about −10 to about 60° C. and a relative humidity of about 10 to about 100%. In the laboratory ambient conditions are typically adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF THE INVENTION

It has been found that the inventive dental composition comprising a hardenable powder can easily be applied to the sulcus using a powder jet device.

The inventive dental composition is typically applied to the sulcus directly, that is, without the aid of a retraction cord or retraction ring as suggested in DE 2 142 756. Thus, the dental composition of the invention does not contain a retraction cord or retraction ring.

Moreover, in certain embodiments the dental composition may have hydrophilic properties and thus can adhere well to hard and soft dental tissue (e.g. gingiva).

Furthermore, in certain embodiments the dental composition may expand during the retraction-procedure and may change its surface to a non-sticking material in respect to tissue, dental restorative or impression materials.

In contrast to the state of the art retraction cords, certain embodiments of the dental composition produce a smooth surface during hardening. This may facilitate an easy removal out of the sulcus. The smooth surface may prevent sticking of the cured composition to coagulated blood which may be present in the sulcus. Sticking often may cause an undesired wound opening and bleeding upon removal of the retraction composition.

Certain embodiments of the inventive dental composition are robust against fluids that might be present in the moist environment of the oral cavity, where the setting of the composition takes place (e.g., the dental retraction composition, especially if hardened, does typically not dissolve or undergo a major change in viscosity in saliva over time of use, e.g. within about 30 min).

Depending on the nature of the hardenable powder used and being present in the dental composition, the dental composition itself may show to some extend hemostatic properties. This feature may contribute to stop bleeding which often can not be prevented when preparing the tooth or tooth stump. In addition, a hemostatic agent can be incorporated into the formulation, if desired. The addition of hemostatic agents may sometimes support the retraction procedure.

If alginate is used as a hardenable powder, the dental composition typically shows features known from alginate wound dressings known in the art. Alginates which can be used are typically non-toxic, non-sensitising, biodegradable and non-allergenic materials, which have good absorption and/or resorption characteristics by the living body. This may be beneficial should residues of the composition (hardened or not hardened) remain in the sulcus. Alginates are sometimes said to be biocompatible, meaning that they do not produce a toxic, injurious, or immunological response in living tissue, and/or biodegradable, meaning that residues of the material can be absorbed or degraded by the living body.

Thus, in certain embodiments of the invention, the hardenable powder being present in the dental composition can be characterized as biocompatible.

The dental composition after hardening has typically a sufficient tensile strength enabling the practitioner to remove the cured or hardened composition out of the sulcus of the patient, ideally in one piece.

The dental composition may have inherent or intrinsic hemostatic properties, at least to some extend, without the need for an additional chemical impregnation.

The dental composition may also have a high absorbing capacity.

The chemical and physical nature of the hardenable powder, which can be used, is not particularly limited. Generally speaking, any hardenable powder which can be applied or dispensed using a powder jet device can be used.

Typically, the hardenable powder can be characterized by at least one or more of the following features:
  a particle size (d90) of at most about 400 μm or of at most about 200 μm or of at most about 100 μm or at most about 80 μm.
  a density (bulk density) of at most about 1.5 g/cm$^3$ or of at most about 1 g/cm$^3$ or of at most about 0.8 g/cm$^3$,
  molecular weight (Mw) in the range of about 20,000 g/mol to about 600,000 g/mol or of about 200,000 g/mol to about 400,000 g/mol or of about 250,000 g/mol to about 350,000 g/mol,
  soluble or swellable in water,
being able to form a gel or paste in the presence of a liquid, especially water.

The particle size can be measured as described in the definition section above. In a certain embodiment, the particle size (d90) is within a range of about 0.1 to about 400 µm or within a range of about 0.5 to about 300 µm or within a range of about 1 to about 200 µm.

Density means bulk density and can be either taken from the product specification or be measured by determining the mass a fixed volume of substance has.

Examples of hardenable powders which can be used include biopolymers such as alginates, collagen, gelatine, chitosan, and synthetic polymers or oligomers such as polymethylacrylates. The hardening process can be started depending on the specific material used e.g. by radiation, chemical agents (ion source or polymerization initiator systems) or temperature.

Alginates, which can be used, are naturally occurring polysaccharides found in brown seaweed. Alginate materials may perform an ion exchange when contacted with wound exudate. Sodium ions found in the wound exudate are very soluble and exchange with the calcium ions which are typically present in the alginate material. Upon saturation of an alginate containing material with a solvent, saliva or would exudate, the alginate containing material is converted into a soft, conformable hydrophilic gel.

The chemical nature of the alginate which can be used for the inventive dental retraction device is not particularly limited, however, the alginates are usually bio-copolymers containing dehydro-D-mannuronic acid and dehydro-L-guluronic acid. Naturally available hydrogel based materials can be preferred. Suitable alginates are alginates from algae. Preferred may also be alginates from algae Laminaria hyperborea. Especially useful are alginates from Laminaria hyperborea Steam and from Lessonia trabeculata. Also synthetic alginates or alginates produced by bacteria having a high guluronate content can be used. Preferred salts of these alginic acids are sodium and potassium salts. Especially preferred is the potassium salt.

Compositions which allow the formation of strong gels (e.g. gels with a high tensile strength) may generally be advantageous.

A particularly preferred class of alginates found to be useful for the present invention has a high guluronate content. A high guluronate (G) content may lead to the formation of strong, sometimes brittle gels with good heat stability, whereas a high mannuronate (M) content may lead to the formation of weaker, sometimes more-elastic gels.

The guluronate content of alginates which can be used can be above about 30 wt.-% or above about 50 wt.-% or above about 60 wt.-% with respect to the weight of the alginate in dry form. The guluronate content of the alginate can be as high as about 80 wt.-% or about 75 wt.-% with respect to the weight of the alginate in dry form. Ranges which have been found to be useful are about 50 to about 80 wt.-% or between about 60 to about 75 wt.-% with respect to the weight of the alginate in dry form.

Moreover, aside form the guluronate content or the ratio of guluronate/mannuronate content, the gelling properties of alginates can be influenced by the crosslinking or hardening agent used.

The molecular weight (Mw) of the alginate is not particularly limited, either, but is typically in a range between about 20,000 to about 600,000 g/mol or between about 200,000 to about 400,000 g/mol or between about 250,000 to about 350,000 g/mol.

The dental composition can be comprised of the hardenable powder only or a mixture of different hardenable powders. However, it is also possible that the dental composition comprises in addition to the hardenable powder one or more additives. Thus, the dental composition can comprise the hardenable powder and additive(s). It is, however, also feasible that the additive(s) are present in a separate liquid, which is to be applied together or independent from the dental composition of the invention.

Additives which can be present in the dental composition include flowing agent(s), filler(s), fiber(s), network builder(s), colourant(s), hemostatic agent(s), anti-microbial agent(s), matting agent(s), flavouring agent(s), sweetening agent(s), hardening agent(s), viscosity modifier(s), pH-stabiliser(s) (buffer), retarder(s), pigment(s), x-ray opaque additive(s) or mixtures thereof.

Additive(s), if present at all, can typically be present in an amount of up to about 90 wt.-% or up to about 80 wt.-% or up to about 50 wt.-%, with respect to the whole composition.

According to one embodiment, the dental composition comprises
    the hardenable powder in an amount of about 5 to about 98 wt.-% or about 20 to about 90 wt.-% or about 30 to about 80 wt.-%,
    additives in an amount of 0 to about 95 wt.-% or 10 to about 80 wt.-% or 20 to about 70 wt.-%, wt.-% with respect to the whole composition.

In certain embodiments of the invention the additives described in the text of the invention can be present only in the dental composition comprising the hardenable powder, or only in a composition comprising a hardening agent or in both compositions, the dental composition and the composition comprising the hardening agent. It is also possible that only a few additives are present in the dental composition and other additives are present in the composition comprising a hardening agent.

According to one embodiment, the dental composition may contain one or different flowing agent(s). If a flowing agent is present, the dispensing or application of the dental composition out of the nozzle of a powder jet device is typically improved.

If a flowing agent is present, it is typically present in a low amount. Amounts, found to be useful, include 0.001 to about 10 wt.-% or about 0.01 to about 5 wt.-% or about 0.1 to about 3 wt.-% with respect to the weight of the whole dental composition.

Examples of flowing agents, which can be used, include fumed silica (e.g. Aerosil™, obtainable from e.g. Degussa Comp., Cab-o-Sil™ TS-530 (160-240 m²/g), manufactured by Cabot Corporation, or HDKH™ (Wacker)) and hollow or solid glass beads (e.g. S60™, iM 30K™ obtainable from 3M Company).

Flowing agents may typically have a particle size d90/µm below about 75 µm, or below about 1 µm or even below about 20 nm.

In another embodiment of the invention, the dental composition may contain filler or a mixture of fillers as additive.

The nature of the filler of the inventive composition is not particularly limited. Anorganic or organic fillers or mixture of both can be used, if desired.

Specific examples of fillers which can be used include quartz, cristobalite, calcium silicate, diatomaceous earth, zirconium silicate, wollastonite (e.g. Tremin™), montmorillonite such as bentonite, talcum, zeolite, including molecular sieves such as sodium aluminium silicate, metal oxide powder of aluminium, titanium, magnesium or zinc or their mixed oxides, barium sulphate, calcium carbonate, plaster, glass and plastic powder.

It has been found to be possible to employ mixtures of silicone dioxides, including those derived form crystalline silicon dioxide, such as pulverized quartz; amorphous silicone dioxides, such as a diatomaceous earth and silanated fumed silica, such as Cab-o-Sil™ TS-530 (160-240 m²/g), manufactured by Cabot Corporation. Varying the sizes and surface areas of the foregoing materials enables one of the cured compositions. Some or all of the foregoing hydrophobic fillers may be surface treated with one or more silanating agents, as known to those of ordinary skill in the art. Such a silanation may be accomplished, e.g., using known halogenated silanes or silazides. Some useful functionalized silicas are commercially available, e.g., products sold under the brands Aerosil™ (Degussa) or HDKH™ (Wacker).

Useful organic fillers include thermoplastic or elastomeric homo- or copolymer particles, e.g. PP (polypropylene), PE (polyethylene), PTFE (polytetrafluoroethylene), PET (polyethylene terephthalate), PA (polyamide), PEEK (polyetheretherketone), PAI (polyamidimide), PI (polyimide), PPS (polyphenylenesulfide), blends thereof, cellulose powders or organic nanofillers like trimethylsilylglucose, cottonweed, carbon black Further organic fillers which can be used include so-called super-absorbers like starch glycolate, (e.g. Ultramyl™) or sodium polyacrylate (Luquasorb™ available from BASF).

The structure of the anorganic and organic materials can be of all shape, including solid or hollow fibres of variable length.

Depending on the nature and amount of filler used, the filler might also fulfil the function of a flowing agent. Even if the chemical nature of the filler or the flowing agent can be the same, flowing agents are typically used in smaller amounts compared to fillers. Moreover, the particle size of flowing agents is typically smaller compared to fillers.

The size of the filler particles should be such that a homogeneous mixture with the hardenable powder can be obtained.

Typically, the size of the filler particles can be in a range of about 20 nm to about 300 μm, or in a range of about 50 nm to about 150 μm or in a range of about 100 nm to about 100 μm. However, in certain embodiments even a particle size below about 20 nm can be suitable.

If a filler is present, it is typically present in an amount of less than about 60 wt.-% or less than about 50 wt.-% or less than about 40 wt.-%. The filler can be present in an amount of 1 to about 60 wt.-% or in an amount of about 5 to about 50 wt.-% or in an amount of about 15 to about 40 wt.-%.

In another embodiment, fibers (e.g. cellulose fibers) can be added. The addition of fibers can be advantageous in some aspects. They may improve the viscosity, they may strengthen the composition and may influence its volume, they may act as a slip additive and binding agent or they may offer improved compressibility. Typically, the addition of fibers can lead to improved moisture and oil retention. Fibers, if present, can also be blended with other ingredients and may act as an additive carrier.

In a specific embodiment the dental composition may comprise as an additive a network builder to enhance mechanical strength, if needed.

Examples of network builders, which can be used, include polyether(s), polyvinyl alcohol derivative(s), polyrotaxane(s), cellulose derivative(s), chitosane derivative(s), cyclodextrine(s), derivatives from hyaluronic acid, polyacrylamide(s) or polymethylacrylamide(s), compounds containing reactive (e.g. polymerizable) residues.

A network builder might not be present at all, but can be present in an amount up to about 25 wt.-% or up to about 50 wt.-% with respect to the weight of the whole dental composition. If a network builder is present, it is typically present in an amount of at least about 3 wt.-% or at least about 10 wt.-% with respect to the weight of the whole dental composition.

In a further embodiment, the dental retraction device has a colour which may allow an easy detection in a patient's mouth (especially compared to oral tissue and/or tooth substance) and control whether after the treatment all residues of the retraction device have been removed from the sulcus. E.g., a blue, green or yellow colour may be suitable. However, in view of some new impression techniques like e.g. digital scanning, other colours might be preferred. Some techniques prefer colours that are less visible for the scanning instrument e.g. red or white. Colouring of the dental composition can be achieved by incorporating colorants or pigments (organic and inorganic) into the composition.

Examples of colourants which can be used include red iron oxide 3395, Bayferrox 920 Z Yellow, Neazopon Blue 807 (copper phthalocyanine-based dye) or Helio Fast Yellow ER.

In a further embodiment the dental composition may comprise one or more hemostatic agents. Hemostatic agents (sometimes also referred to as astringent agents) that may be useful in assisting hemostasis include, but are not limited to oxides, chloride or sulphate salts of ferrum (e.g. ferric sulfate, ferric subsulfate, ferric chloride), aluminium (e.g. potassium aluminum sulfate, aluminum ammonium sulfate, aluminum sulfate, aluminum chlorohydrate, aluminum acetate) and zinc, polyphenols, ellag acid, permanganates (e.g. potassium permanganate), silver nitrate and hydrogen peroxide and mixtures thereof. One preferred class of hemostatics include aluminum compounds.

Suitable biopolymers and polysaccharides, which might contribute to a hemostatic effect include cellulose, celluloses derivates, gelatine, starch, starch derivates, collagen, alginate, chitin, chitosan, or hyaloron acid and mixtures thereof.

Physically effective hemostyptica include phytogenic or mineral zeolites, micro porous polysaccharide spheres, kaolin and celite.

Pharmaceutical drugs which might contribute to a hemostatic effect include adrenaline, epinephrine, propylhexedrine, adrenochrom-monosemicarbazone propylgallat, tranexamic acid, etamsylate, batroxobin, thrombin, fibrin dressings.

If a hemostatic agent is present, it is typically present in an amount of about 0.01 wt.-% to about 25 wt.-% or in an amount of about 0.1 wt.-% to about 15 wt.-% or in an amount of about 0.5 wt.-% to about 5 wt.-% with respect to the weight of the whole dental composition.

In another embodiment, the dental composition comprises an anti-microbial agent. This might help reducing health risks for professionals in the dental offices and laboratories as well as for patients caused by bleeding prior impression taking caused by drilling or retracting the gingival cuff. It may reduce the risk of contamination of the patient having a wound as well as the risk of contamination of the impression taken, thus preventing contamination of dental professionals in the dental office as well as of the dental lab.

To provide an efficient and time-saving solution the dental composition can contain the anti-microbial component when delivered to the dentist. The dental retraction device can also contain an astringent agent in addition.

It can be beneficial, if residues of the dental composition which were left in the sulcus by accident do not interfere with or negatively affect the setting reaction of the impression material used after the retraction procedure.

It is known that some hemostatics which are used in solution or together with retraction cords (the cord may be impregnated or soaked in the solution prior use) can compromise the setting reaction of certain impression materials.

For instance, as indicated in the instruction of use of certain impression materials, epinephrine (adrenaline), 8-hydroxyquinoline sulfate or iron (III) sulfate may impair the setting behaviour.

Therefore, it can be an advantage, if the anti-microbial agent used is compatible with the impression material to be used and does not compromise the setting behaviour thereof.

Furthermore, it can be advantageous to use combinations of anti-microbial compounds to generate an additive or synergistic effect.

Useful combinations include chlorhexidine or derivatives thereof and aldehydes (glutaraldyde, phtaldehyde) and chlorhexidine or its derivatives and salts of phenolics or acids. It can also be preferred to use acid adducts of chlorhexidine or its derivatives like e.g., acetates, chlorides, nitrates, sulfates or carbonates.

Chlorhexidine and its derivatives (hereinafter referred to as CHX) are commercially available in water-based solutions (e.g. a 20% aqueous solution of CHX digluconate, CAS18472-51-0) or as a pure compound or as a salt. As additive to non-water based impression materials the pure compound (CAS 55-56-1) and CHX salts like CHX diacatate monohydrate (CAS 56-95-1) or CHX dihydrochloride (CAS 3697-42-5) are preferred.

CHX also seems to be especially suited as an additive due in part to its well-known and proven anti-microbial action against Gram positive and Gram negative microorganisms including the oral Streptococci and Lactobacilli. CHX is bacteriostatic for Mycobaterium. CHX is also active against yeasts including Candida albicans and viruses including HIV, HBV, HCV, Influenza- and Herpes virus. A further advantage of CHX is its low toxicity.

Preferred anti-microbial agents include: Hexitidin, Cetypyridiniumcloride (CPC), Chlorhexidin (CHX), chlor amine T, Triclosan, stannous chloride, benzalkonium chloride, non-ionic or ionic surfactants (e.g. quarternary ammonium compounds), alcohols [monomeric, polymeric, mono-alcohols, poly-alcohols (e.g. Xylitol, Sorbitol), aromatic (e.g. phenol)], antimicrobial peptides (e.g. histatins), bactericins (e.g. nisin), antibiotics (e.g. tetracycline), aldehydes (e.g. glutaraldehyde) inorganic and organic acids (e.g. bencoic acid, salicylic acid, fatty acids) or there salts, derivative of such acids such as esters (e.g. p-hydroxy benzoate or other parabenes, lauricidin), enzymes (e.g. lysozyme, oxidases), proteins (e.g. enamel matrix protein, prolin rich proteins), fluoride, EDTA, essential oils (e.g. thymol). Several silver containing components are reported to have an antimicrobial effect, too.

An example of a useful combination of an anti-microbial agent and an astringent agent is aluminium chloride or partially neutralized aluminium chloride and CHX dichloride.

If an anti-microbial agent is present, it is typically present in an amount of about 0.01 wt.-% to about 5 wt.-% or in an amount of about 0.1 wt.-% to about 1 wt.-% with respect to the weight of the whole dental retraction device in dry form.

In another embodiment a vasoconstrictor such as epinephrine and/or propylhexedrine can be added.

According to a further embodiment, the dental composition of the invention can also contain a hardening agent. A hardening agent is an agent being able to at least partially initiate or start the hardening of the hardenable powder being present in the dental composition.

The nature of the hardening agent, if used, is not particularly limited unless an unwanted reaction between the dental composition to be applied and the hardening agents takes place. Moreover, hardening agents which might be detrimental to the patient's health or might be damaging to the powder jet device are typically not used.

Hardening agents, which can be used, include chemical curing agents (including initiators comprising peroxide and amine(s)), light curing agents (including initiators comprising campher chinone and amine(s)) or ionic curing agents (including initiators comprising di- or trivalent ion sources) like plaster or other calcium salts. Generally, any salt (organic or inorganic) can be used, which is able to dissociate into di- or poly-valent cations in an amount efficient to start the setting reaction of the dental composition of the invention.

According to one embodiment of the invention, the hardening agent is selected from a di- or trivalent ion source. The nature of the poly-di- or trivalent ion source is not particularly limited. In principle any di- or trivalent ion source can be used being able to form a temporary or permanent complex with the alginate. Ions forming irreversible complexes with the alginates are preferred. Ions which can be used include ions selected from Ca, Ba, Zn, Co, Mn, Cu, Al, Zr, Ti, Si, Ag and Fe or mixtures thereof.

The nature of the counter ion is not particularly limited, either. Counter ions found to be useful are phosphate, hydrogenphosphate, sulfate, carbonate, fluoride, chloride, bromide, oxalate, acetate, succinate, citrate, or ascorbate. The di- or trivalent ion source may contain in addition crystal water.

From the divalent ions calcium is sometimes preferred. A preferred source of calcium ions are good soluable calcium salts like calcium sulfate, calcium acetate, calcium chloride, calcium oxalate or calcium ascorbate or complexes of calcium with EDTA. Barium carbonate, copper(II) carbonate in which crystal water might be incorporated are also useful divalent ion sources.

One possibility of producing the dental composition described in the text of the invention is combining, blending or mixing the respective components of the dental composition. In particular, the hardenable powder is mixed with the additive(s), if present. Mixing can be accomplished by hand or by using a mixing machine such as tumblers, mills or speedmixers. The dental composition has to be in a form or shape enabling the dental composition to be applied with a powder jet device into the sulcus between soft and hard dental tissue.

If desired, the components to be mixed can be milled first until an appropriate particle size is achieved. Milling can be accomplished using a ball mill, an air impact mill or others. Using an air separator or sieves can be beneficial to facilitate extracting suitable particle sizes from the (milled) powder.

The nature of the powder jet device to be used for the application of the dental composition comprising a hardenable powder is not particularly limited, either. In principle, any powder jet device being able to dispense powders can be used.

Powder jet devices are well known to the practitioner and are currently used for cleaning tooth surfaces.

Typically, the powder jet device comprises a handpiece and a reservoir for storing the dental composition comprising the hardenable powder prior, during and after the use. The reservoir can be part of the handpiece or can be part of a separate basis station of the powder jet device.

The handpiece typically comprises a nozzle and can be connected to the basis station of the powder jet device or to the dental chair unit using a flexible tube. Thus, it is also possible that the powder jet device is basically comprised of the handpiece only.

Examples of powder jet devices, which can be used, include those described e.g. in GB 2 026 359 A, U.S. Pat. No. 3,972,123 or U.S. Pat. No. 4,676,749. The content of each of these documents with respect to the description of powder jet devices, handpieces and nozzles is herewith incorporated by reference and considered part of the description of the present invention.

Powder jet devices, which can be used and which are commercially available, include Airflow S 1 (EMS S.A.), PROPHYflex 3 (KaVo Dental GmbH) and Cavitron PROPHY-JET (Dentsply DeTrey GmbH).

The dental composition is typically applied using gas or a gas stream. The nature of the gas which can be used is not particularly limited unless an unwanted reaction between the dental composition to be applied and the gas stream takes place. Moreover, gases which might be detrimental to the patient's health or might be damaging to the powder jet device are typically not used.

Gas which can be used include air, nitrogen, argon, carbon dioxide or mixture of one or more of these gases.

The pressure of the gas is typically in a range of about 0.5 to about 10 bar or of about 1 and about 8 bar or of about 2 and about 6 bar or 3 to about 5 bar.

The dental composition can be applied together with a liquid, if desired. The nature of the liquid which can be used is not particularly limited, either, unless an unwanted reaction between the dental composition to be applied and the liquid takes place. Moreover, liquids which might be detrimental to the patient's health or might be damaging to the powder jet device are typically not used.

Liquids which can be used include water, alcohols, especially low boiling alcohols including ethanol, and ketones including acetone and mixtures of one or more of these liquids. Typically, water is preferred.

If a liquid is used, the liquid might be able to partially or fully dissolve the hardenable powder being present in the dental composition, that is, at least a part of the dental composition might be soluble in the liquid. In another embodiment, however, the liquid used is not able to dissolve the dental composition completely, but can form a dispersion or an emulsion with the dental composition, especially with the hardenable powder being present in the dental composition. The liquid might also be able to form a gel with the hardenable powder or the dental composition containing the hardenable powder or causes the hardenable powder or the dental composition containing the hardenable powder to swell.

If the powder jet device is used to apply a liquid and the dental composition, the liquid can be applied either together with the gas or separately from the gas. In the latter case, the handpiece of the powder jet device has typically different orifices in the nozzle, one orifice for the gas, one orifice for the powder and one orifice for the liquid.

According to another embodiment of the invention, the liquid and/or the dental composition can comprise a hardening agent being able to at least initiate hardening of the hardenable powder being present in the dental composition. Hardening agents, which can be used, include those which have already been described in the text of the invention.

Upon addition or application of the hardening agent to the curable composition or to at least a part of the surface thereof, the setting process of the curable composition is started.

A solution or liquid containing a hardening agent can comprise other additives as well. Principally, all additives which might be present in the dental composition described in the text of the present invention can also be present in the solution containing the hardening agent.

Such additives include flowing agent(s), filler(s), fiber(s), network builder(s), colorant(s), hemostatic agent(s), anti-microbial agent(s), anti-evaporation agent(s), flavouring agent(s), viscosity modifier(s), preserving agent(s), polymer(s), fluoride(s), sweetening agent(s), x-ray opaque additive(s) and mixtures thereof.

According to a further embodiment of the invention, a hardening agent (optionally together with one or more additives described in the text of the invention) can be applied independently from the application of a liquid. Thus, a hardening agent can be applied in a separate step before, during or after the application of the dental composition comprising the hardenable powder to the tooth structure. The application of the hardening agent can be repeated, if desired.

If the dental composition of the invention comprising the hardenable powder is cured or hardened (e.g. by applying or using a hardening agent as described in the text of the invention), the cured or hardened composition can typically be characterized by the following feature:
    tensile strength (determined according to ISO 37 (as described in more detail below) of at least about 0.4 MPa or at least about 0.5 MPa or at least about 0.6 MPa.

Another embodiment of the invention is directed to a kit of parts comprising
    a dental composition comprising a hardenable powder as described in the text of the invention,
    a hardening agent for the hardenable powder,
    optionally a handpiece of a powder jet device,
    optionally a powder jet device and
    optionally retraction caps.

As outlined in the text of the present invention, a powder jet device is typically equipped with a handpiece. The handpiece is typically reversible connectable via a (flexible) tube to the basis station of the powder jet device or to the dental chair unit equipped with a pressurized air/liquid unit. Thus, in certain embodiments, the handpiece is an object, which can be separated from the powder jet device and can be purchased independently from the powder jet device. The handpiece might comprise a reservoir for storing the dental composition described in the text of the invention.

The kit may further comprise accessories like retraction caps. Retraction caps can be useful for keeping the retraction material in place until an impression is taken or pushing the curable or cured dental retraction composition into the sulcus. Retraction caps can be made of soft, tissue friendly material, e.g. cotton. However, other materials might be useful as well. If appropriate a temporary restoration or a customized impression can be used as retraction cap, too. Commercially available retraction caps are e.g. sold under the brand Comprecap™ or Roeko Comprecap™ Anatomic (Coltène Whaledent).

The dental composition comprising the hardenable powder described in the text of the invention is preferably provided to the practitioner under hygienic conditions. One possibility to achieve this is packing the dental composition in a sealed container including sealable bottles, vessels or foil bags (including glass or plastic bottles, e.g. equipped with a screw cap).

The dental composition and a suitable hardening agent, optionally together with an appropriate hand piece of a powder jet device (if desired together with some replacement nozzles) can be packaged and sold together in a so-called introduction kit.

A further embodiment of the invention is directed to a method for retracting dental tissue comprising the steps of
    optionally applying a composition comprising a hardening agent,
    applying a dental composition comprising a hardenable powder with a powder jet device into the sulcus between soft and hard dental tissue, optionally applying a composition comprising a hardening agent, leaving the dental composition in the sulcus for a time appropriate to effect retraction of the soft dental tissue, removing the dental composition from the sulcus.

The term "optionally" indicates that this process step is not mandatory, but can be applied, if desired. Thus, the application of a crosslinker composition can be done before the dental composition comprising the hardenable powder is applied or after this step or before and after this step. If the hardening agent is part of the liquid, the application of the hardening agent can take place more or less simultaneously during the application of the powder.

If a hardening agent is used during the process of the application of the dental composition comprising the hardenable powder, the hardenable powder is typically brought into contact with the hardening agent, causing the hardenable powder or a gel formed by the hardenable powder to harden.

The term "bringing into contact" means that the hardening agent is at least applied to at least a part of the surface of the dental composition or vice a versa. The step of "bringing into contact" can be accomplished e.g. by dipping, spraying or brushing.

The sequence of the application steps is equal and independent from each other and can also be repeated, if desired. Thus, according to one embodiment of the invention, the dental composition is provided or applied first, followed by the application of the hardening agent or a composition comprising a hardening agent.

The dental composition is typically left in the sulcus for an appropriate time. It is basically up to the practitioner to decide whether the time is appropriate or not, in view of the fact that this time range can vary from patient to patient. Usually, the cured dental composition is left in the sulcus until the desired retraction of the soft dental tissue is achieved.

A time range of at least about 30 s (seconds) or at least about 1 min (minute) or at least about 5 min can be appropriate. Typically, the dental composition is removed from the sulcus (after application) within a time range of about 15 min or about 10 min or about 8 min.

The above process comprises the steps of placing, applying or bringing the dental composition into the sulcus between soft and hard dental tissue. In some cases compression caps or bridges, temporary crowns or bridges or even a first impression might be used as a kind of accessory during the retraction process. The dental composition may remain in the sulcus for a couple of minutes (e.g. about 1 to about 10 or about 2 to about 6 min) to achieve effective mechanical retraction.

Preferably, the dental composition can be fast and easily applied to the sulcus and removed after curing there from, if possible, in one piece.

Upon application of the hardening agent or composition containing the hardening agent to at least a part of the surface of the curable dental composition, the latter one begins to set resulting typically in a high viscous gel, which usually does not show a flowing behaviour anymore under the conditions in the patient's mouth.

The setting or curing reaction can typically be accomplished within a short period of time. Typically, the setting reaction is completed within about 5 min or within about 1 min or within about 10 s or even within about 5 s. The term "completed" within this context means that the composition does not undergo further alterations with regard to viscosity visible to the human eye.

Typically, the hardenable powder used in the dental composition does not contain components which are damaging to the tooth structure, especially the soft tooth structure (e.g. dentin).

Thus, certain embodiments of the dental composition are essentially free of abrasive particles (e.g. particles in a size or shape that can provide significant abrasion when used with the recommended pressure like $NaHCO_3$) or do not contain abrasive particles at all.

A substance can be classified as abrasive within the meaning of the invention, if it causes significant abrasion (also on soft tooth tissue, e.g. dentin) when it is applied in the instructed manner.

A test method, which can be used to find out whether a certain substance is abrasive or not, is described in U.S. Pat. No. 6,648,644 B1, column 3 to 4. For the present invention, an abraded volume of more than about 0.1 $mm^3$ is considered to be damaging for the dentin tooth structure.

The following examples are given to illustrate, but not limit, the scope of this invention. Unless otherwise indicated, all parts and percentages are by weight.

Examples

If not reported otherwise, all tests were conducted at ambient conditions (23° C.; 50% humidity and room pressure) and all % are wt.-%.

Materials

The following materials were used (Table 1):

TABLE 1

| Name | Description | Availability |
| --- | --- | --- |
| KF 200 S | potassium alginate | FMC Polymer |
| calcium sulphate dihydrate | $CaSO_4 * 2 H_2O$ | Aldrich |
| sodium polyphosphate | | Aldrich |
| Aerosil ™ A 380 | fumed silica | Degussa |
| Talcum | water containing magnesium silicate | Talkum Bergbau |
| Celatom ™ | flux calcined diatomaceous earth | Chemag |
| Ultramyl ™ | Sodium starch glycolate | Gustav Parmentier |
| Luquasorb ™ 1010 | Superabsorbent polymer | BASF |
| Kaolin | hydrated aluminum silicates | Aldrich |
| Bentonite | aluminium phyllosilicate, consisting mostly of montmorillonite | Aldrich |
| S60, iM30K | Glass bubbles | 3M Comp. |
| OP 278 | matting agent | Degussa |

Typical Synthesis of a Dental Composition Containing a Hardenable Powder

The respective components as delivered were mixed in a speedmixer DAC 150 FVZ (Hauschild Comp.).

Device

The powder jet device used for the application of the dental composition was an Airflow™ device (available from EMS S.A. Company). The device was equipped with a nozzle having two orifices, one for the powdery substance to be applied together with gas and one for liquid.

Method of Application

The respective powder or mixture of powders was filled into the powder reservoir of the powder jet device. The gas used for the application of the powder was air (gas pressure: 3 to 6 bar). The liquid, which was applied simultaneously with the powder, was water or aqueous calcium chloride solution (10 wt.-%).

The dental composition was tested using in an in vitro test with a Frasaco™ Standard Model AG3 (Frasaco Comp.) and self-created sulcus models based on gingival mask material or hydrocolloid material.

Measurements

Viscosity

The viscosity was evaluated using a rheometer MCR 300 manufactured by Anton Paar equipped with a 8 mm parallel plate geometry with flat surfaces. The tests were performed at 23° C. The temperature was controlled within 0.1° C. by a Peltier element in the lower plate. The measurement gap was constant at 0.2 mm.

The measurement was performed at a permanent increasing medial shear rate between 0 and $2\ s^{-1}$. The rheometer recorded one data point per $0.1\ s^{-1}$ step and each measurement point lasted for 10 seconds. In the table below, the value for a shear rate of $0.3\ s^{-1}$ is reported. All materials were measured two times.

Tensile Strength and Elongation at Break

The method was done in accordance with ISO 37 with a slightly variance of test specimens.

For testing alginate pastes the thickness of the dumb-bell test piece type 2 was reduced from 2 mm down to 0.5 mm. The measurements were performed with a universal test machine (UPM Z020, Zwick). Before testing, the dies were filled with paste and the surface of the paste moistened with the 20% calcium chloride solution as hardening agent (amount of hardening agent used: 0.5 ml hardening agent per 0.5 g of dental retraction composition). The specimens were allowed to cure for 90 s (seconds) at 23° C. and at 50% relative humidity before testing. The test velocity was 200 mm/min and the force sensor was calibrated up to 5 kN. Tensile strength and elongation at break values were determined.

Reference pastes were prepared by mixing the respective components and the resulting compositions analysed with respect to mechanical data according to the process described above (Table 2).

TABLE 2

| Paste | Components | Tensile strength [MPa] | Elongation at break [%] | Viscosity [Pa*s] |
|---|---|---|---|---|
| 1 | 20% KF 200S 80% water | 2.03 (SD 0.36) | 78.78 (SD 11.99) | 15,000 |
| 2 | 20% KF 200S 79.7% water 0.3% Aerosil 380 | 1.08 (SD 0.45) | 65.71 (SD 17.69) | 16,050 |

SD: standard deviation

Table 3 below summarizes the dental compositions tested. All dental compositions showed sufficient flowability during the application process.

TABLE 3

| Powder | Components | [wt.-%] | Observation |
|---|---|---|---|
| 1 | KF 200 S | 55 | hardening |
|   | calcium sulfate dihydrate | 35 | |
|   | sodium polyphosphate | 9.9 | |
|   | Aerosil A 380 | 0.1 | |
| 2 | KF 200 S | 99.7 | hardening upon application of $CaCl_2$ |
|   | Aerosil A 380 | 0.3 | |
| 3 | KF 200 S | 55 | hardening |
|   | calcium sulfate dihydrate | 35 | |
|   | sodium polyphosphate | 9.7 | |
|   | S60 | 0.3 | |

TABLE 3-continued

| Powder | Components | [wt.-%] | Observation |
|---|---|---|---|
| 4 | KF 200 S | 55 | hardening |
|   | calcium sulfate dihydrate | 35 | |
|   | sodium polyphosphate | 9.7 | |
|   | iM 30K | 0.3 | |
| 5 | KF 200 S | 55 | hardening |
|   | Calcium sulfate dihydrate | 35 | |
|   | sodium polyphosphate | 9.7 | |
|   | OP 278 | 0.3 | |
| 6 | KF 200 S | 55 | hardening |
|   | calcium sulfate dihydrate | 35 | |
|   | sodium polyphosphate | 9.7 | |
|   | talcum M 30 | 0.3 | |
| 7 | KF 200 S | 49.7 | hardening upon application of $CaCl_2$ |
|   | Celatom | 50 | |
|   | Aerosil A 380 | 0.3 | |
| 8 | Powder 1 | 95 | hardening |
|   | Ultramyl | 5 | |
| 9 | Powder 1 | 70 | hardening |
|   | Ultramyl | 30 | |
| 10 | Powder 1 | 95 | hardening |
|   | Luquasorb 1010 | 5 | |
| 11 | Powder 1 | 70 | hardening |
|   | Luquasorb 1010 | 30 | |
| 12 | Powder 2 | 95 | hardening upon application of $CaCl_2$ |
|   | Kaolin | 5 | |
| 13 | Powder 2 | 70 | hardening upon application of $CaCl_2$ |
|   | Kaolin | 30 | |
| 14 | Powder 2 | 95 | hardening upon application of $CaCl_2$ |
|   | Bentonite | 5 | |
| 15 | Powder 2 | 70 | hardening upon application of $CaCl_2$ |
|   | Bentonite | 30 | |

The invention claimed is:

1. A method for retracting dental tissue comprising the steps of
    a) applying a dental composition comprising a hardenable powder with a powder jet device into the sulcus between soft and hard dental tissue,
    b) applying a composition comprising a hardening agent either before or after step a)
    c) leaving the dental composition in the sulcus for a time sufficient to effect retraction of the soft dental tissue,
    d) removing the dental composition from the sulcus.

2. The method of claim 1, wherein the dental composition comprises a hardenable powder to be used in a process for retraction of dental tissue, wherein the dental composition does not comprise a retraction cord or retraction ring.

3. The method according to claim 2, wherein the hardenable powder is characterized by at least one of the following features:
    a molecular weight (Mw) in the range of about 20,000 g/mol to about 600,000 g/mol,
    a grain size between about 0.1 to about 400 µm (d90),
    a bulk density of at most about 1.5 $g/cm^3$,
    swellable or able to form a gel or paste in the presence of a liquid.

4. The method according to claim 2, wherein the hardenable powder is selected from alginate(s), collagen, gelatine(s), chitosan(s), polymethylacrylates and mixtures thereof.

5. The method according to claim 4, wherein the dental composition comprises at least one additive selected from flowing agent(s), filler(s), fiber(s), network builder(s), colourant(s), hemostatic agent(s), anti-microbial agent(s), hardening agent(s), viscosity modifier(s), buffer(s), retarder(s), x-ray opaque additive(s) and mixtures thereof.

6. The method according to claim 5, wherein the dental composition comprises the hardenable powder in an amount of about 5 to about 98 wt.-%, additive(s) in an amount of about 2 to about 95 wt.-%, with respect to the weight of the whole composition.

7. The method according to claim 1, wherein the dental composition is applied or dispensed using gas and/or a liquid.

* * * * *